US012614888B2

(12) United States Patent　　　　(10) Patent No.:　US 12,614,888 B2
Cho et al.　　　　　　　　　　　　(45) Date of Patent:　Apr. 28, 2026

(54) LASER APPARATUS

(71) Applicant: LUTRONIC CORPORATION, Goyang-si (KR)

(72) Inventors: Wook Rae Cho, Goyang-si (KR); Jin Hu Lee, Goyang-si (KR); Min Jee Jeon, Bucheon-si (KR)

(73) Assignee: LUTRONIC CORPORATION, Goyang-si (KR)

( * ) Notice: Subject to any disclaimer, the term of this patent is extended or adjusted under 35 U.S.C. 154(b) by 990 days.

(21) Appl. No.: 17/908,743

(22) PCT Filed: Dec. 10, 2020

(86) PCT No.: PCT/KR2020/018102

§ 371 (c)(1),
(2) Date: Sep. 1, 2022

(87) PCT Pub. No.: WO2021/118280

PCT Pub. Date: Jun. 17, 2021

(65) Prior Publication Data

US 2024/0072509 A1　　Feb. 29, 2024

(30) Foreign Application Priority Data

Dec. 13, 2019　(KR) ........................ 10-2019-0167151

(51) Int. Cl.
H01S 3/109　　　　(2006.01)
A61B 18/00　　　　(2006.01)
　　　　(Continued)

(52) U.S. Cl.
CPC .............. H01S 3/109 (2013.01); A61B 18/20 (2013.01); H01S 3/0071 (2013.01);
　　　　(Continued)

(58) Field of Classification Search
CPC . A61B 2018/207; H01S 3/0809; H01S 3/107; H01S 3/109
See application file for complete search history.

(56) References Cited

U.S. PATENT DOCUMENTS 7,773,643 B2　8/2010　Masuda
2002/0024978 A1*　2/2002　Inagaki ................... H01S 3/139
　　　　　　　　　　　　　　　　372/20
(Continued)

FOREIGN PATENT DOCUMENTS

JP　　　　2010-54547 A　　3/2010
KR　　10-2008-0088440 A　　10/2008
(Continued)

OTHER PUBLICATIONS

Korean Notice of Allowance for 10-2019-0167151 dated, Apr. 7, 2021.
(Continued)

*Primary Examiner* — Michael Carter
(74) *Attorney, Agent, or Firm* — Sughrue Mion, PLLC

(57)　　　　ABSTRACT

Disclosed is a laser apparatus including a laser generator comprising a laser medium, a pumping light source providing light to the laser medium, a first mirror and a second mirror arranged with the laser medium therebetween, and configured to generate a laser beam of a first wavelength, a secondary harmonic wave generator configured to generate a laser beam of a second wavelength from the laser beam of a first wavelength, a light modulator arranged between the laser medium and the secondary harmonic wave generator and configured to adjust a pulse width of the laser beam of a first wavelength, and an output adjustor configured to adjust an output of the laser beam of a second wavelength generated in the secondary harmonic wave generator.

17 Claims, 9 Drawing Sheets

(51) Int. Cl.

| | | |
|---|---|---|
| *A61B 18/20* | (2006.01) | |
| *H01S 3/00* | (2006.01) | |
| *H01S 3/08* | (2023.01) | |
| *H01S 3/10* | (2006.01) | |
| *H01S 3/107* | (2006.01) | |

(52) U.S. Cl.
CPC ........ *H01S 3/0809* (2013.01); *H01S 3/10053* (2013.01); *H01S 3/10061* (2013.01); *H01S 3/107* (2013.01); *A61B 2018/00458* (2013.01)

(56) References Cited

U.S. PATENT DOCUMENTS

| | | | | | |
|---|---|---|---|---|---|
| 2002/0138072 | A1* | 9/2002 | Black | .................... | A61B 18/22 |
| | | | | | 606/17 |
| 2006/0108337 | A1* | 5/2006 | Gu | ........................ | B23K 26/40 |
| | | | | | 219/121.61 |
| 2012/0051375 | A1* | 3/2012 | Karpushko | ............. | H01S 3/109 |
| | | | | | 372/22 |
| 2017/0100041 | A1* | 4/2017 | Kasamatsu | ........ | G01N 29/0654 |

FOREIGN PATENT DOCUMENTS

| | | | |
|---|---|---|---|
| KR | 10-2015-0101081 | A | 9/2015 |
| KR | 10-2019-0052796 | A | 5/2019 |
| KR | 10-2019-0054668 | A | 5/2019 |
| KR | 20190054668 | * | 5/2019 |

OTHER PUBLICATIONS

Korean Office Action for 10-2019-0167151 dated, Oct. 7, 2020.
International Search Report for PCT/KR2020/018102 dated, Mar. 16, 2021 (PCT/ISA/210).
Written Opinion of International Searching Authority or PCT/KR2020/018102 (PCT/ISA/237).

* cited by examiner

LASER APPARATUS

CROSS REFERENCE TO RELATED APPLICATIONS

This application is a National Stage of International Application No. PCT/KR2020/018102 filed Dec. 10, 2020, which claims priority to Korean Patent Application No. 10-2019-0167151 filed Dec. 13, 2019 in the Korean Intellectual Property Office, the disclosures of which are incorporated herein by reference in their entireties.

TECHNICAL FIELD

Embodiments of the present disclosure relate to a laser apparatus.

BACKGROUND ART

Laser beams have been used in various fields for an industrial use, a medical use, a military use, and the like. In particular, a laser apparatus for a medical use, which is capable of locally concentrating certain energy and performing a non-invasive treatment, has been widely used in surgery, internal medicine, ophthalmology, dermatology, dentistry, and the like.

In the treatment using a laser apparatus, a laser beam of a different energy level depending on a treatment area or a location, in other words, the depth from skin, is necessary. A laser beam of a short wavelength may be generated by being converted from a laser beam of a long wavelength. In this state, the form of an output varies depending on input pumping energy, and it may be difficult to maintain a beam shape constant.

DESCRIPTION OF EMBODIMENTS

Technical Problem

Provided is a laser apparatus which may exhibit excellent beam quality by forming a laser beam of a short wavelength in a wavelength conversion method.

Provided is a laser apparatus which may output a multi-wavelength laser beam.

Solution to Problem

According to an aspect of the present disclosure, a laser apparatus including a laser generator comprising a laser medium, a pumping light source providing light to the laser medium, a first mirror and a second mirror arranged with the laser medium therebetween, and configured to generate a laser beam of a first wavelength, a secondary harmonic wave generator configured to generate a laser beam of a second wavelength from the laser beam of a first wavelength, a light modulator arranged between the laser medium and the secondary harmonic wave generator and configured to adjust a pulse width of the laser beam of a first wavelength, and an output adjustor configured to adjust an output of the laser beam of a second wavelength generated in the secondary harmonic wave generator.

The secondary harmonic wave generator may include the second mirror, a non-linear medium, and a third mirror facing the second mirror with the non-linear medium therebetween.

The output adjustor may include a phase delayer configured to change a phase of the laser beam of a second wavelength, and a polarizer arranged on an optical path passing the phase delayer.

The phase delayer may include an element that adjusts a degree of a phase delay of incident light, by being rotated according to an input signal.

The laser apparatus may further include a driving mirror arranged on an optical path between the secondary harmonic wave generator the output adjustor, and configured to be driven to be on or out of the optical path to allow the laser beam of a second wavelength to be output by passing through the output adjustor or not.

A polarizer may not be arranged on a path between the laser medium and the non-linear medium, and the laser beam of a first wavelength may be incident on the non-linear medium in a non-polarization state.

The laser medium may generate a laser beam of a 1064 nm wavelength, and the secondary harmonic wave generator may generate a laser beam of a 532 nm wavelength.

According to another aspect of the present disclosure, a laser apparatus includes a laser generator including a first mirror, a laser medium, and a pumping light source that provides light to the laser medium, the laser generator being configured to a laser beam of a first wavelength, a secondary harmonic wave generator configured to generate a laser beam of a second wavelength from the laser beam of a first wavelength, and including a non-linear medium, and a second mirror and a third mirror arranged with the non-linear medium therebetween, a light modulator arranged between the laser medium and the secondary harmonic wave generator and configured to adjust a pulse width of the laser beam of a first wavelength, a driving mirror arranged on an optical path between the laser medium and the light modulator, having a total reflection surface inclined with respect to the optical path, and configured to be driven to be on or out of the optical path, a fourth mirror arranged on an optical path along which light reflected from the driving mirror travels, an output adjustor configured to adjust an output of the laser beam of a second wavelength generated in the driving secondary harmonic wave generator, and one or more optical path adjustment optical elements configured to match an output path when the laser beam of a first wavelength or the laser beam of a second wavelength is output according to a location of the driving mirror.

The one or more optical path adjustment optical elements may be configured to output the laser beam of a first wavelength when the driving mirror is on the optical path, and the laser beam of a second wavelength when the driving mirror is moved out of the optical path.

When the driving mirror is on the optical path, the first mirror and the fourth mirror may form a resonance path to generate the laser beam of a first wavelength, and when the driving mirror is moved out of the optical path, the first mirror and the third mirror may form a resonance path to generate the laser beam of a first wavelength.

The one or more optical path adjustment optical elements may include a fifth mirror configured to reflect light having transmitted the fourth mirror in a perpendicular direction, a sixth mirror configured to reflect light having passed through the output adjustor in the perpendicular direction, and a first beam splitter configured to transmit light reflected from the fifth mirror, and reflect light reflected from the sixth mirror in the perpendicular direction.

The one or more optical path adjustment optical elements may include a seventh mirror and an eighth mirror arranged between the light modulator and the secondary harmonic wave generator and configured to sequentially and respectively reflect incident light in a perpendicular direction, a ninth mirror and a tenth mirror arranged between the secondary harmonic wave generator and the output adjustor and configured to sequentially and respectively reflect incident light in the perpendicular direction, and a second beam splitter configured to reflect light having transmitted the fourth mirror in the perpendicular direction and transmit light having passed through the output adjustor.

The laser apparatus may further include an optical fiber arranged on the output path, and a focusing lens arranged on the output path and configured to focus light on the optical fiber.

The output adjustor may include a phase delayer configured to change a phase of the laser beam of a second wavelength, and a polarizer arranged on the optical path after the phase delayer.

No polarizer may be arranged between the laser medium and the non-linear medium, and the laser beam of a first wavelength may be incident on the non-linear medium in a non-polarization state.

According to another aspect of the present disclosure, a treatment apparatus includes any one of the laser apparatus described above, and a controller configured to select a wavelength mode of the laser apparatus and drive the laser apparatus in a selected mode.

The laser beam of a second wavelength may be used for treatment of superficial vascular lesions or pigmented lesions, and the laser beam of a first wavelength may be used for treatment of lesions at a relatively deep position.

The laser beam of a second wavelength may include a laser beam of a 532 nm wavelength, and may be used for any one of epidermal pigment, blemishes, pigmentation, flat warts, age spots, freckles, blood vessel removal, and flushing.

The laser beam of a first wavelength may include a laser beam of a 1064 nm wavelength, and may be used for any one of toning for improving skin texture, wrinkles, pores, face tone, or scar, vein vessel removal, hair removal, acne erythema improvement, pore shrinkage, skin lifting, skin fine wrinkle removal, and inflammatory acne treatment.

Advantageous Effects of Disclosure

The above-described laser apparatus may form a laser beam of a short wavelength in a wavelength conversion method, and have various outputs of excellent beam quality.

The above-described laser apparatus may selectively output a multi-wavelength laser beam, and exhibit excellent beam quality with respect to various pulse widths and output energies.

The above-described laser apparatus may be used as a treatment apparatus because a laser beam suitable for the location or shape of a treatment target lesion can be selected.

MODE OF DISCLOSURE

Figure 1:
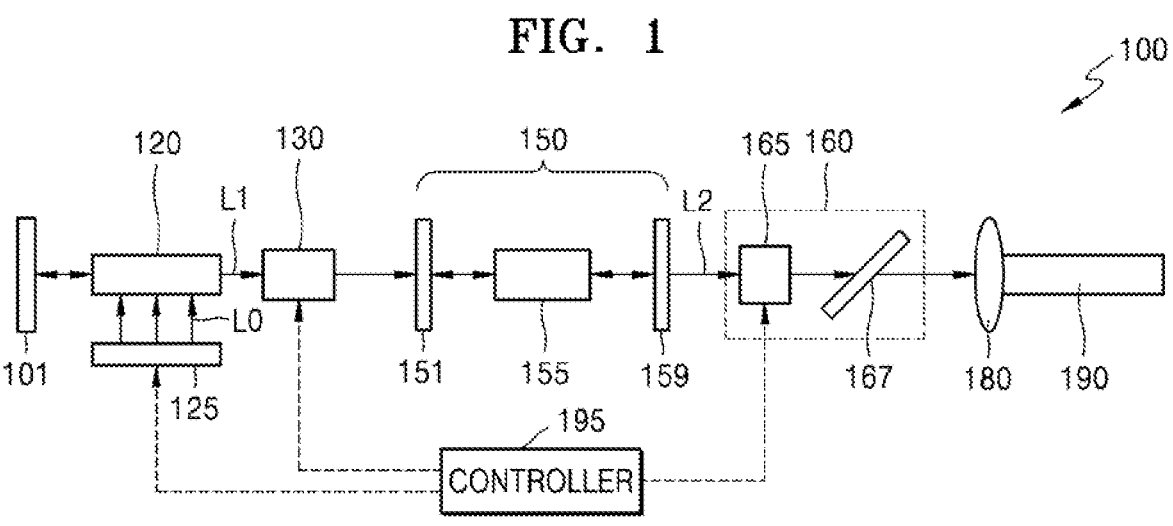
FIG. 1 is a schematic view showing the optical arrangement of a laser apparatus according to an embodiment.

Various modifications may be applied to the present embodiments, and particular embodiments will be illustrated in the drawings and described in the detailed description section. The effect and features of the present embodiments, and a method to achieve the same, will be clearer referring to the detailed descriptions below with the drawings. However, the present embodiments may be implemented in various forms, not by being limited to the embodiments presented below.

Hereinafter, exemplary embodiments will be described in detail with reference to the accompanying drawings, and in the description with reference to the drawings, the same or corresponding constituents are indicated by the same reference numerals and redundant descriptions thereof are omitted.

In the following embodiment, a number, for example, first, second, and the like, used in the description of an embodiment is merely an identification sign to distinguish one constituent element from another constituent element.

In the following embodiment, the expression of singularity in the specification includes the expression of plurality unless clearly specified otherwise in context.

In the following embodiment, it will be further understood that the terms "comprises" and/or "comprising" used herein specify the presence of stated features or components, but do not preclude the presence or addition of one or more other features or components.

In the following embodiment, it will be understood that when a layer, region, or component is referred to as being "formed on" another layer, region, or component, it can be directly or indirectly formed on the other layer, region, or component. That is, for example, intervening layers, regions, or components may be present.

Sizes of components in the drawings may be exaggerated for convenience of explanation. For example, since sizes and thicknesses of components in the drawings are arbitrarily illustrated for convenience of explanation, the following embodiments are not limited thereto.

When a certain embodiment may be implemented differently, a specific process order may be performed differently from the described order. For example, two consecutively described processes may be performed substantially at the same time or performed in an order opposite to the described order.

In the following embodiment, it will be understood that when a layer, region, or component is referred to as being "connected to" another layer, region, or component, it can be directly connected to the other layer, region, or component or indirectly connected to the other layer, region, or component via intervening layers, regions, or components.

Figure 2:
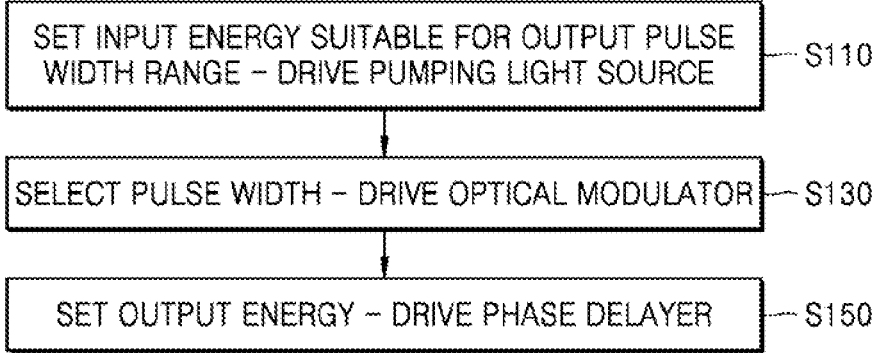
FIG. 2 is a flowchart schematically showing the driving of the laser apparatus of FIG. 1.

FIG. 1 is a schematic view showing the optical arrangement of a laser apparatus according to an embodiment, and FIG. 2 is a flowchart schematically showing the driving of the laser apparatus of FIG. 1.

A laser apparatus 100 may include a laser medium 120 that receives energy and generates a laser beam L1 of a first wavelength, a secondary harmonic wave generator 150 that generates a laser beam L2 of a second wavelength from the laser beam L1 of a first wavelength, an light modulator 130 that is arranged between the laser medium 120 and the secondary harmonic wave generator 150 and adjusts the pulse width of the laser beam L1 of a first wavelength, and an output adjustor 160 that adjusts the output of the laser beam L2 of a second wavelength generated in the secondary harmonic wave generator 150.

The laser apparatus 100 according to an embodiment employs an optical configuration capable of outputting the laser beam L2 of a second wavelength with various output energies, and furthermore, guaranteeing excellent beam quality, when generating the laser beam L2 of a second wavelength by converting the wavelength of the laser beam L1 of a first wavelength. A detailed configuration thereof is described below.

A pumping light source 125 provides light L0 to the laser medium 120. The pumping light source 125 may include a flash lamp. However, the disclosure is not limited thereto, and the pumping light source 125 may include other light sources, for example, a laser diode. The pumping light source 125 is controlled by a controller 195, and receives power from a power supply unit that is not shown and emits light so that the light L0 is provided to the laser medium 120.

The laser medium 120 absorbs energy of the light provided from the pumping light source 125 and emits amplified light. The laser medium 120 may include neodymium-doped yttrium aluminum garnet (Nd:Yag), but the disclosure is not limited thereto, and neodymium: yttrium-aluminum-perovskite (Nd:YAP) may be used as the laser medium 120.

A first mirror 101 is arranged at one side of the laser medium 120. The first mirror 101 forms a part of a laser resonator, and may be a mirror that totally reflects the light beam of a first wavelength.

The light modulator 130 may be configured as a Q-switch including an acoustic light modulator or an electro-light modulator. The light modulator 130 may be configured as a Pockels cell. The Pockels cell is electrically controlled and may be operated in a mode of maintaining the phase of incident light or a mode of delaying the phase of incident light. The light modulator 130 is controlled by the controller 195, controls the phase of incident light according to an applied electrical signal, and may adjust the pulse width of the laser beam L1 of a first wavelength to a desired width. The pulse width means the width of a pulse train occurring by summing the widths of individual single pulses. The width of an individual single pulse may be several tens to hundreds of nanoseconds. The width of a pulse train composed of the pulses of nano-units may range, for example, 0.3 ms to 40 ms, but the disclosure is not limited thereto.

Typically, when a pulse is formed in a Q-switching method, an output form varies depending on input pumping energy so that it is difficult to maintain a constant beam shape. In order to maintain a constant beam shape, the laser apparatus 100 according to an embodiment sets input energy suitable for an output pulse width range and accordingly drives the pumping light source 125. For example, the pumping light source 125 may be fixed to a value at which the maximum output can be obtained with respect to each pulse width.

The secondary harmonic wave generator 150 may include a non-linear medium 155, and a second mirror 151 and a third mirror 159 arranged to face each other with the non-linear medium 155 therebetween.

The second mirror 151 may be a mirror that transmits light of a first wavelength, and reflects light of other wavelengths. The second mirror 151 may be a mirror that, for example, performs an anti-reflection function on the light of a first wavelength and totally reflects the light of a second wavelength. The third mirror 159 may be a mirror that transmits the light of a second wavelength and reflects light of other wavelengths. The third mirror 159 may be a mirror that, for example, performs an anti-reflection function on the light of a second wavelength and totally reflects the light of a first wavelength.

The non-linear medium 155 is arranged between the second mirror 151 and the third mirror 159 and may perform frequency doubling of the frequency of light. The non-linear medium 155 may include, for example, second harmonic generation (SHG) crystal. The non-linear medium 155 may include, for example, KTP or LBO. On the optical path between the second mirror 151 and the third mirror 159, the laser beam L1 of a first wavelength is converted into the laser beam L2 of a second wavelength and then may transmit the third mirror 159. In other words, the light that has not been converted to the second wavelength is reflected from the third mirror 159 toward the non-linear medium 155, and repeats the optical path of being reflected from the second mirror 151. The light converted into the second wavelength on the repeated path transmits the third mirror 159, that is, is output from the secondary harmonic wave generator 150. The first wavelength may be 1064 nm, and the second wavelength may be 532 nm. However, but the disclosure is not limited thereto.

The laser apparatus 100 according to an embodiment, unlike a polarized beam of a 1064 nm wavelength is generally needed to oscillate a 532 nm wavelength in the existing structure, a polarizer is not provided in the resonator, that is, between the laser medium 120 and the non-linear medium 155, and the laser beam L1 of a first wavelength that is non-polarized is incident on the non-linear medium 155. Due to the structure, a depolarization loss by the polarizer does not occur.

Furthermore, in the frequency conversion using a non-linear material, a frequency conversion efficiency increases as the strength of input energy increases. In the existing structure, to increase the intensity of light incident on a non-linear material, a mirror or focusing lens having a concave reflecting surface may be provided, but when strong energy is focused on a limited position, the non-linear material may be damaged. The laser apparatus 100 according to an embodiment, in which the pumping energy input to the secondary harmonic wave generator 150 may be fixed to be the maximum output, may not cause damage to the non-linear medium 155 and may increase the frequency conversion efficiency.

The output of the laser beam L2 of a second wavelength generated in the secondary harmonic wave generator 150 may be adjusted by passing through the output adjustor 160. The output adjustor 160 may include a phase delayer 165 and a polarizer 167. The phase delayer 165 may be an element that is controlled according to an input signal and adjusts a degree of the phase delay of incident light. The phase delayer 165 may be operated as a $\frac{1}{4}$ wave plate, a $\frac{1}{2}$ wave plate, or a wave plate of other multiples according to electrical control. The polarizer 167 may transmit only a certain polarization component of the incident light. For example, light of a polarization parallel to a polarization axis formed in the polarizer 167 is transmitted and light of other polarizations are not transmitted. Under the control of the phase delayer 165, light is incident on the polarizer 167 after the amount of a polarization component parallel to the polarization axis is adjusted, so that an output thereof is adjusted.

The phase delayer 165 may be an element that can be driven to be rotated according to an electrical signal. A degree of delaying the phase of incident light may vary according to the degree of rotation. However, the phase delayer 165 is not limited thereto, and may be an element including a material having optical properties changes according to an electrical signal.

The laser apparatus 100 may further include an optical fiber 190 and a focusing lens 180 for focusing light on the optical fiber 190, which are arranged on an output path. The laser beam L2 of a second wavelength may be transmitted to a position where the laser beam L2 of a second wavelength is to be used, via the optical fiber 190.

The operation of the controller 195 that controls laser apparatus 100 is briefly described with reference to FIG. 2. Input energy suitable for an output pulse width range is set, and accordingly, the pumping light source 125 may be driven (S110). The input energy may be fixed as energy for the maximum output. The laser apparatus 100 selects a pulse width to output, and accordingly, the light modulator 130 may be driven (S130). Furthermore, according to the desired output energy, a phase delayer included in the output adjustor 160 may be controlled (S150). As such, the laser apparatus 100 may output the laser beam L2 of a second wavelength having desired pulse width and output. The pulse width of the laser beam L2 of a second wavelength, that is, the width of a pulse train composed of nano-unit pulses, may be implemented to be about 40 ms.

Figure 3:
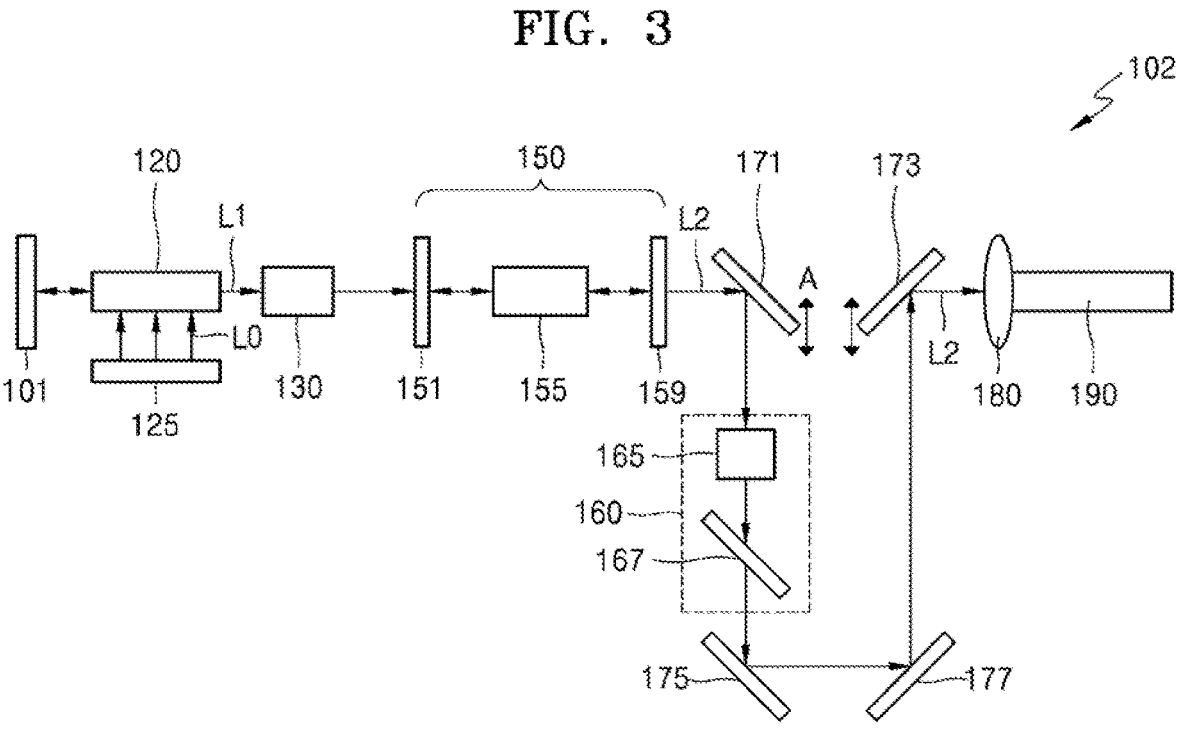
FIGS. 3 and 4 are schematic views showing the optical arrangement of a laser apparatus according to another embodiment, in which laser light is output through different optical paths.
Figure 4:
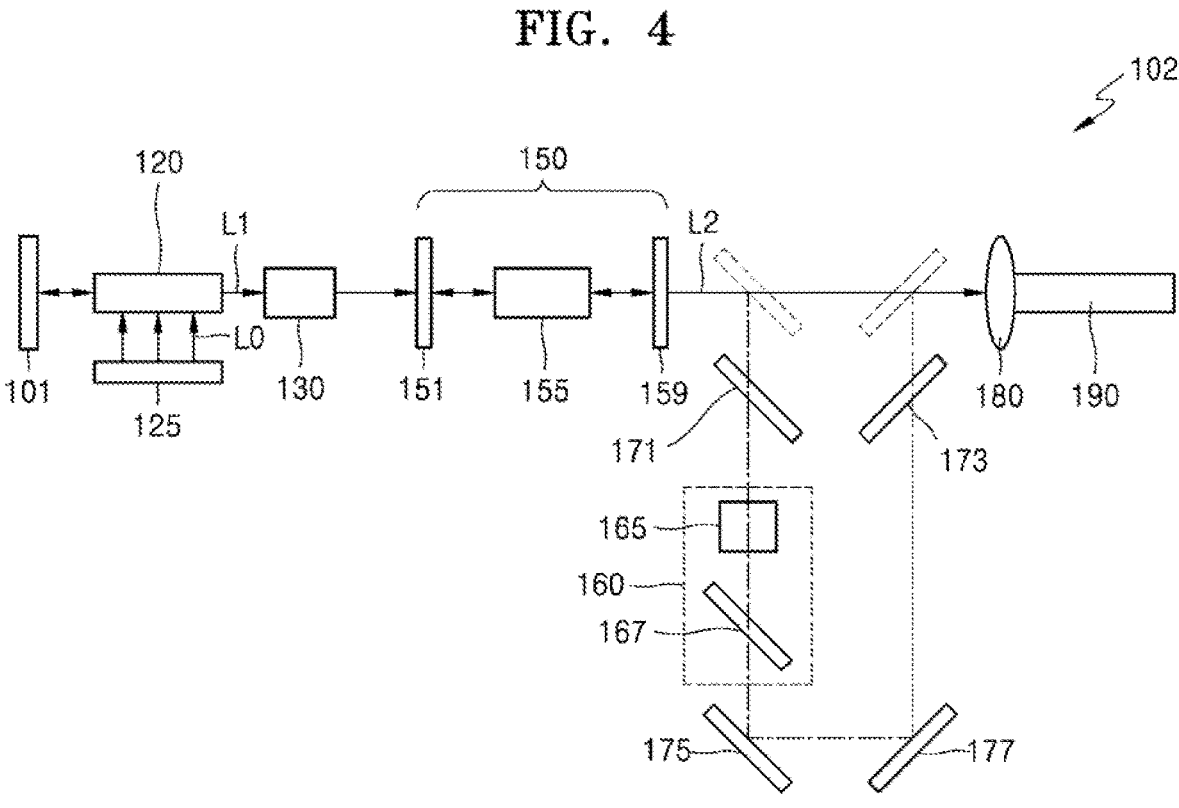

FIGS. 3 and 4 are schematic views showing the optical arrangement of a laser apparatus according to another embodiment, in which laser light is output through different optical paths.

A laser apparatus 102 according to the present embodiment is different from the laser apparatus 100 of FIG. 1 in that driving mirrors 171 and 173 are further provided on the optical path between the secondary harmonic wave generator 150 and the output adjustor 160, and the other configurations are substantially the same. The illustration of the controller 195 is omitted for convenience.

The driving mirrors 171 and 173 may be driven to move in a direction perpendicular to the optical axis, for example, a direction indicated by an arrow A. According to the driving of the driving mirrors 171 and 173, the laser beam L2 of a second wavelength may be output by passing through the output adjustor 160 or not passing therethrough.

As illustrated in FIG. 3, when the driving mirrors 171 and 173 are arranged in the path of the light generated and output from the secondary harmonic wave generator 150, the laser beam L2 of a second wavelength may be output by passing through the output adjustor 160.

As illustrated in FIG. 4, when the driving mirrors 171 and 173 are arranged outside the path of the light generated and output from the secondary harmonic wave generator 150, the laser beam L2 of a second wavelength is output without passing through the output adjustor 160.

For the laser beam L2 of a second wavelength that having passed through the output adjustor 160 or not having passed therethrough, to be output on the same output path, mirrors 175 and 177 for adjusting the direction of the light passing through the output adjustor 160 may be further provided.

When not passing through the output adjustor 160, the laser beam L2 of a second wavelength of the maximum output may be output, and when passing through the output adjustor 160, the laser beam L2 of a second wavelength in which the maximum output is adjusted to a desired degree may be output.

Figure 5:
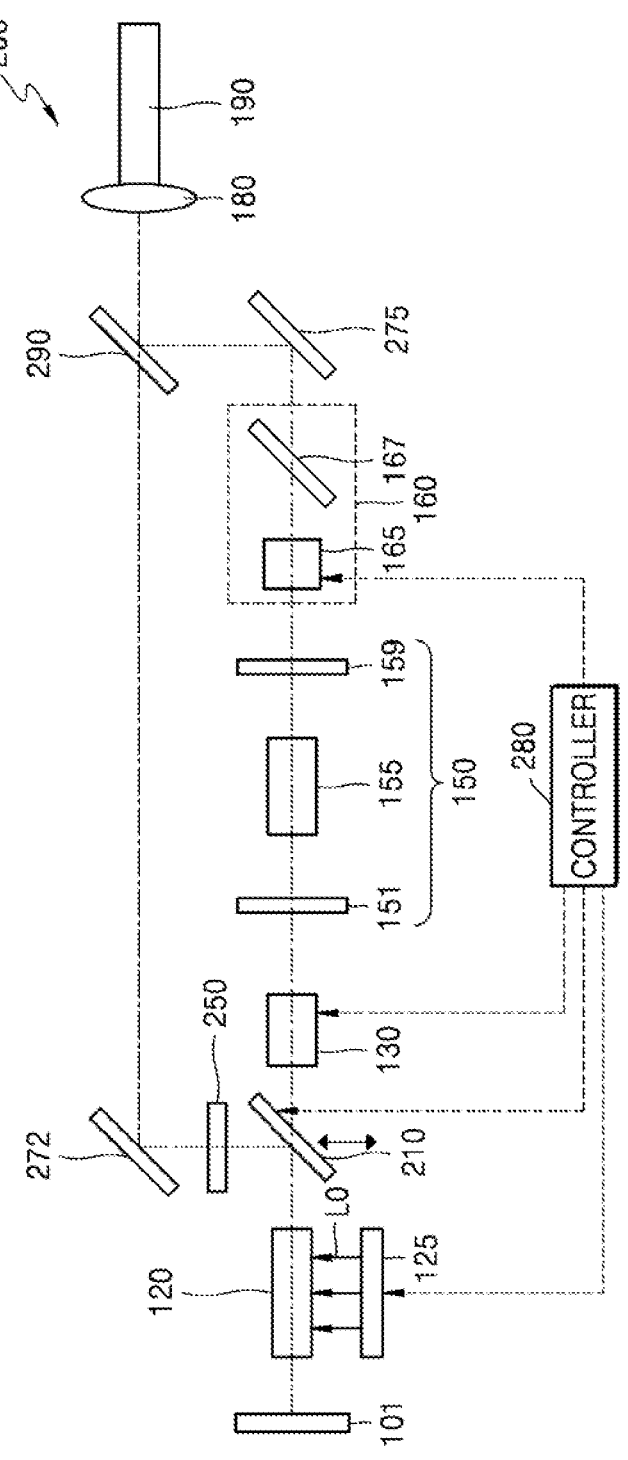
FIG. 5 is a schematic view showing the optical arrangement of a laser apparatus according to another embodiment.
Figure 6A:
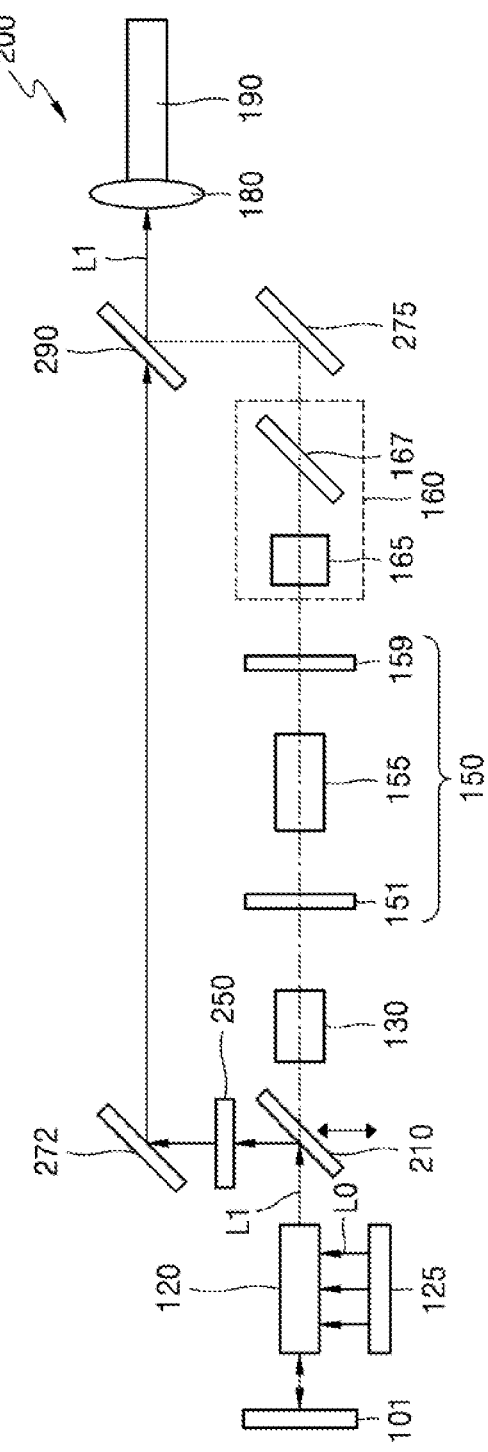
FIGS. 6A and 6B respectively illustrate an optical path when the laser apparatus of FIG. 5 outputs a laser beam of a first wavelength and an optical path when the laser apparatus of FIG. 5 outputs a laser beam of a second wavelength.
Figure 6B:
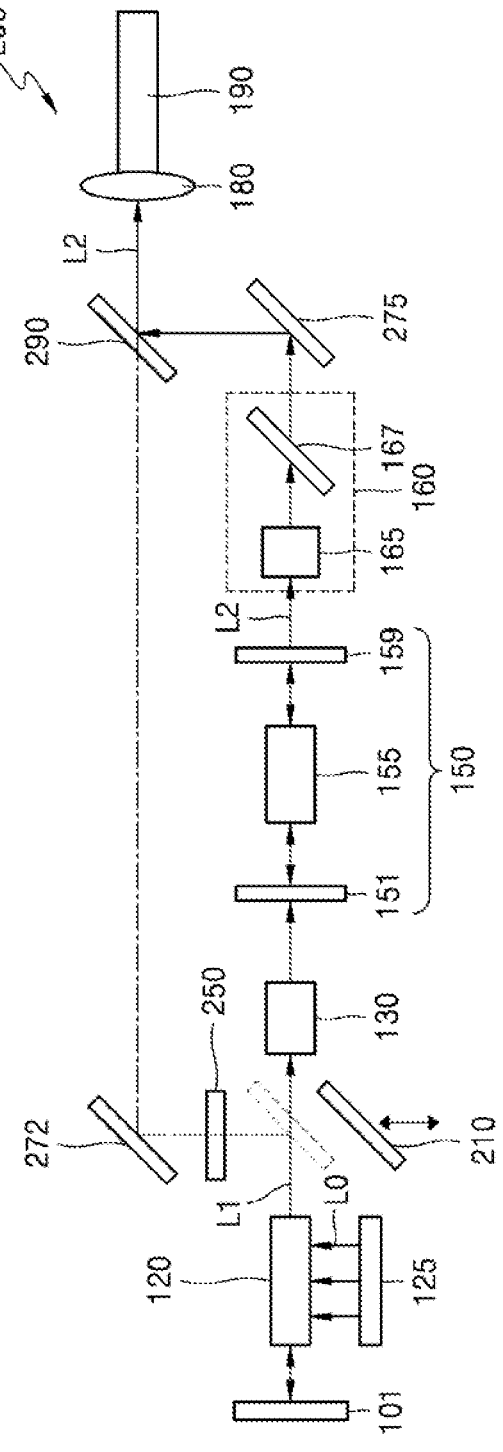

FIG. 5 is a schematic view showing the optical arrangement of a laser apparatus according to another embodiment. FIGS. 6A and 6B respectively illustrate an optical path when the laser apparatus of FIG. 5 outputs a laser beam of a first wavelength and an optical path when the laser apparatus of FIG. 5 outputs a laser beam of a second wavelength.

A laser apparatus 200 according to the present embodiment has an optical arrangement in which the laser beam L1 of a first wavelength or the laser beam L2 of a second wavelength are selectively output.

Referring to FIG. 5, the laser apparatus 200 may include a laser generator including the first mirror 101, the laser medium 120, and the pumping light source 125 for providing light to the laser medium 120, and generating a laser beam of a first wavelength, the secondary harmonic wave generator 150 generating the laser beam L2 of a second wavelength from the laser beam L1 of a first wavelength and including the second mirror 151, the non-linear medium 155, and the third mirror 159, the light modulator 130 arranged between the laser medium 120 and the secondary harmonic wave generator 150 and adjusting the pulse width of a laser beam of a first wavelength, and the output adjustor 160 adjusting the output of the laser beam L2 of a second wavelength generated in the secondary harmonic wave generator 150.

The laser apparatus 200 may further include a driving mirror 210 arranged on an optical path between the laser medium 120 and the light modulator 130, having a total reflection surface inclined to the optical path, and driven to positions on or out of the optical path, and a fourth mirror 250 arranged on the optical path along which light reflected from the driving mirror 210 travels.

The laser apparatus 200 may further include one or more optical path adjustment optical elements that match an output path when the laser beam L1 of a first wavelength or the laser beam L2 of a second wavelength is output according to the location of the driving mirror 210, and a controller 280 that controls the pumping light source 125, the driving mirror 210, the light modulator 130, and the phase delayer 165.

Referring to FIG. 6A, when the driving mirror 210 is on a path of the light from the laser medium 120, the laser beam L1 of a first wavelength is output from the laser apparatus 200. In this case, the first mirror 101 and the fourth mirror 250 form a resonance path for generating the laser beam L1 of a first wavelength.

The fourth mirror 250 may be a mirror that transmits light of a first wavelength and reflects light of other wavelengths. A fifth mirror 272 may be arranged on a path along which the light having transmitted the fourth mirror 250 travels. The fifth mirror 272 may include a total reflection surface arranged to reflect incident light in the perpendicular direction.

Referring to FIG. 6B, when the driving mirror 210 is moved to be located out of the path of the light from the laser medium 120, the laser beam L2 of a second wavelength is output from the laser apparatus 200. In this mode, the first mirror 101 and the second mirror 151 form a resonance path for generating a laser beam of a first wavelength. The laser beam L1 of a first wavelength passes through the light modulator 130 and is incident on the secondary harmonic wave generator 150, and the laser beam L2 of a second wavelength is generated and output from the secondary harmonic wave generator 150. The laser beam L2 of a second wavelength may have output energy adjusted while passing through the output adjustor 160. A sixth mirror 275 may be arranged on a path of the light having passed through the output adjustor 160. The sixth mirror 275 may have total reflection surface arranged to reflect incident light in the perpendicular direction.

When the laser beam L1 of a first wavelength and the laser beam L2 of a second wavelength are selectively output according to a mode, a first beam splitter 290 may be provided to match the output paths of the two laser beams to face the optical fiber 190 at a certain position. The first beam splitter 290, as illustrated in FIG. 6A, may transmit the laser beam L1 of a first wavelength reflected from the fifth mirror 272. The first beam splitter 290, as illustrated in FIG. 6B, may reflect the laser beam L2 of a second wavelength reflected from the sixth mirror 275. The first beam splitter 290 may be configured as a wavelength selective beam splitter that transmits the light of a first wavelength and reflects the light of a second wavelength, according to the operation described above. However, the disclosure is not limited thereto, and when the laser beam L1 of a first wavelength and the laser beam L2 of a second wavelength are controlled to have different polarizations, a polarization beam splitter may be employed as the first beam splitter 290.

According to the structure, the laser apparatus 200 may selectively output the laser beam L1 of a first wavelength or the laser beam L2 of a second wavelength, and furthermore, exhibit excellent beam quality with respect to the laser beam L2 of a second wavelength that is wavelength-converted and output. The laser beam L1 of a first wavelength may have a long pulse made of a single pulse and the pulse width thereof may be implemented to about 60 ms. The laser beam L2 of a second wavelength may have a pulse train composed of nano-unit pulses and the width of the pulse train may be implemented to about 40 ms. The laser apparatus 200 may exhibit a stable output with respect to the laser beam L2 of a second wavelength having various pulse widths, for example, an output of a clinically significant level is possible in a range of 0.3 ms to 0.7 ms that is short pulse width. In this point, the laser apparatus 200 according to an embodiment is different from existing long pulse laser equipment that implement a pulse with of about 1 ms to 30 ms, in which implementable energy decreases as a pulse width increases.

Figure 7:
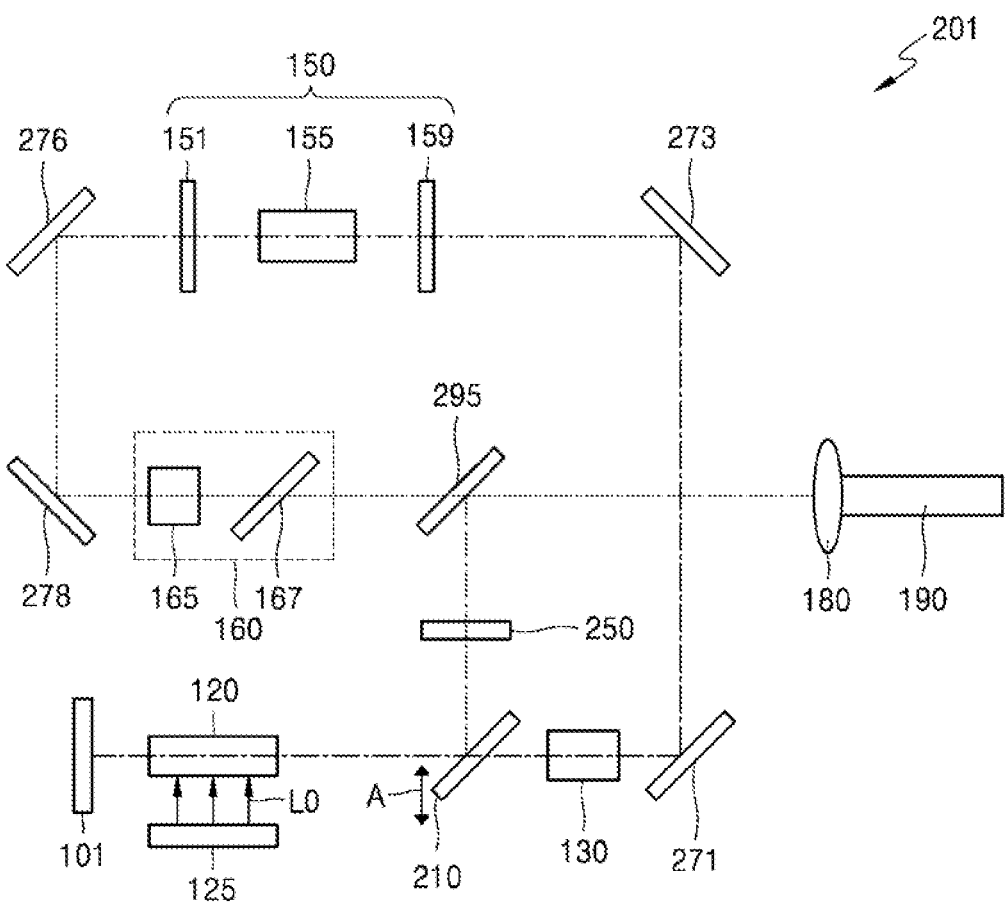
FIG. 7 is a schematic view showing the optical arrangement of a laser apparatus according to another embodiment.
Figure 8A:
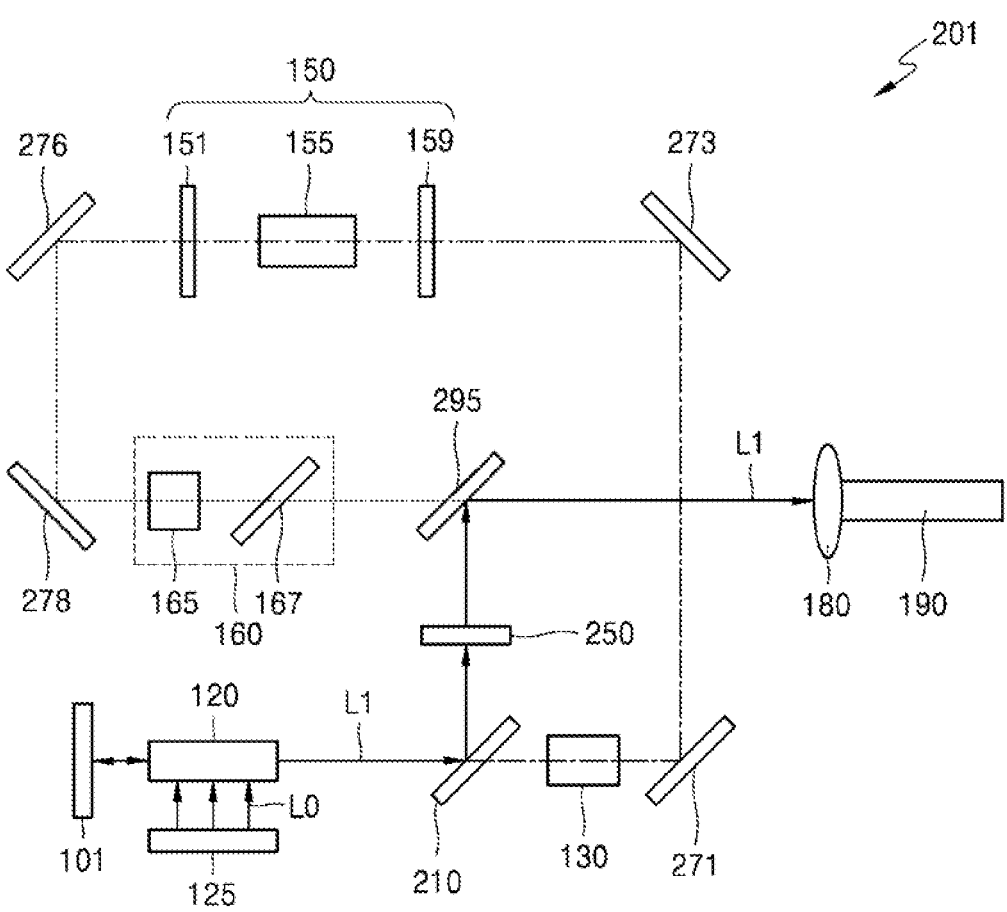
FIGS. 8A and 8B respectively illustrate an optical path when the laser apparatus of FIG. 5 outputs a laser beam of a first wavelength and an optical path when the laser apparatus of FIG. 7 outputs a laser beam of a second wavelength.
Figure 8B:
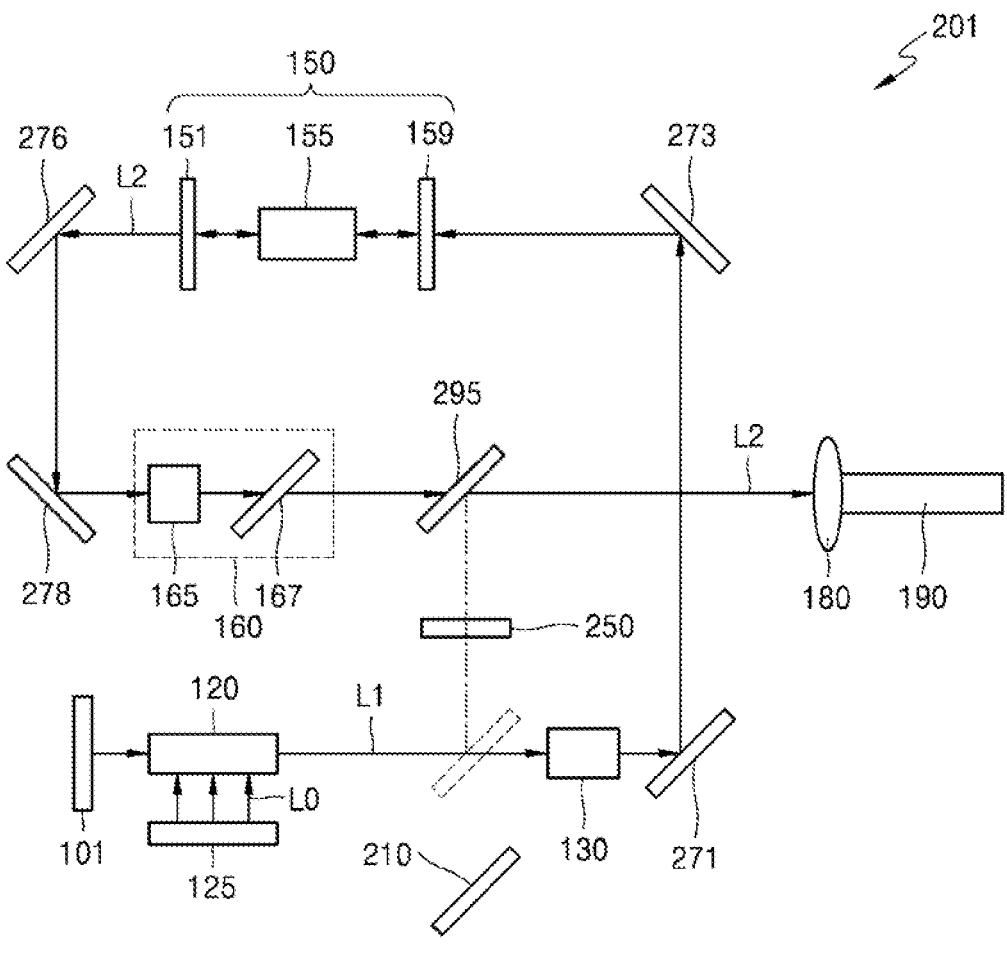

FIG. 7 is a schematic view showing the optical arrangement of a laser apparatus according to another embodiment. FIGS. 8A and 8B respectively illustrate an optical path when the laser apparatus of FIG. 5 outputs a laser beam of a first wavelength and an optical path when the laser apparatus of FIG. 7 outputs a laser beam of a second wavelength.

A laser apparatus 201 of the present embodiment is also a laser apparatus that selectively outputs the laser beam L1 of a first wavelength or the laser beam L2 of a second wavelength, and is different from the laser apparatus 200 of FIG. 5 in a detailed optical path.

Referring to FIG. 8A, when the driving mirror 210 is on a path of the light from the laser medium 120, the laser beam L1 of a first wavelength generated in the laser medium 120 is reflected from the driving mirror 210, the fourth mirror 250, and a second beam splitter 295 and travel toward the optical fiber 190.

Referring to FIG. 8B, when the driving mirror 210 moves so as to be out of the path of the light from the laser medium 120, the laser beam L1 of a first wavelength is wavelength-converted in the secondary harmonic wave generator 150 and the laser beam L2 of a second wavelength is output toward the optical fiber 190. To form the optical path, a seventh mirror 271 and an eighth mirror 273 may be arranged between the light modulator 130 and the secondary harmonic wave generator 150 to sequentially and respectively reflect incident light in the perpendicular direction. Furthermore, a ninth mirror 276 and a tenth mirror 278 may be arranged between the secondary harmonic wave generator 150 and the output adjustor 160 to sequentially and respectively reflect incident light in the perpendicular direction. The light having passed through the output adjustor 160 transmit the second beam splitter 295 and travels toward the optical fiber 190.

The seventh mirror 271, the eighth mirror 273, the ninth mirror 276, and the tenth mirror 278 may each include a total reflection surface that reflects incident light in the perpendicular direction. The second beam splitter 295, as illustrated in FIG. 8A, may reflect the light of a first wavelength, and as illustrated in FIG. 8B, may transmit the light of a second wavelength. The second beam splitter 295 may be configured as a wavelength selective beam splitter that reflects the light of a first wavelength and transmits the light of a second wavelength. However, the disclosure is not limited thereto, and when the laser beam L1 of a first wavelength and the laser beam L2 of a second wavelength are controlled to have different polarizations, a polarization beam splitter may be employed as the second beam splitter 295.

According to the structure, the laser apparatus 201 may selectively output the laser beam L1 of a first wavelength or the laser beam L2 of a second wavelength, and furthermore, exhibit excellent beam quality with respect to the laser beam L2 of a second wavelength that is wavelength-converted and output.

In the present embodiment, an example optical path may be changed differently. For example, the location of the secondary harmonic wave generator 150 may be changed to be between the seventh mirror 271 and the eighth mirror 273 or between the ninth mirror 276 and the tenth mirror 278. Alternatively, the location of the output adjustor 160 may be changed to be between the ninth mirror 276 and the tenth mirror 278. In addition, according to the location of the driving mirror 210, a change to various different paths is possible, in which the laser beam L1 of a first wavelength and the laser beam L2 of a second wavelength are selectively output.

According to the structure, the laser apparatus 201 may selectively output the laser beam L1 of a first wavelength or the laser beam L2 of a second wavelength, and furthermore, exhibit excellent beam quality with respect to the laser beam L2 of a second wavelength that is wavelength-converted and output. The laser beam L1 of a first wavelength may have a long pulse made of single pulse, and the pulse width thereof may be implemented to about 60 ms. The laser beam L2 of a second wavelength may have a pulse train composed of nano-unit pulses and the width of the pulse train may be implemented to about 40 ms.

The laser apparatus according to an embodiment may be used as various apparatuses, for example, medical apparatuses for beauty or treatment. In addition, the laser apparatus according to an embodiment may be employed in various electronic apparatuses capable of selectively using a multi-wavelength laser.

Figure 9:
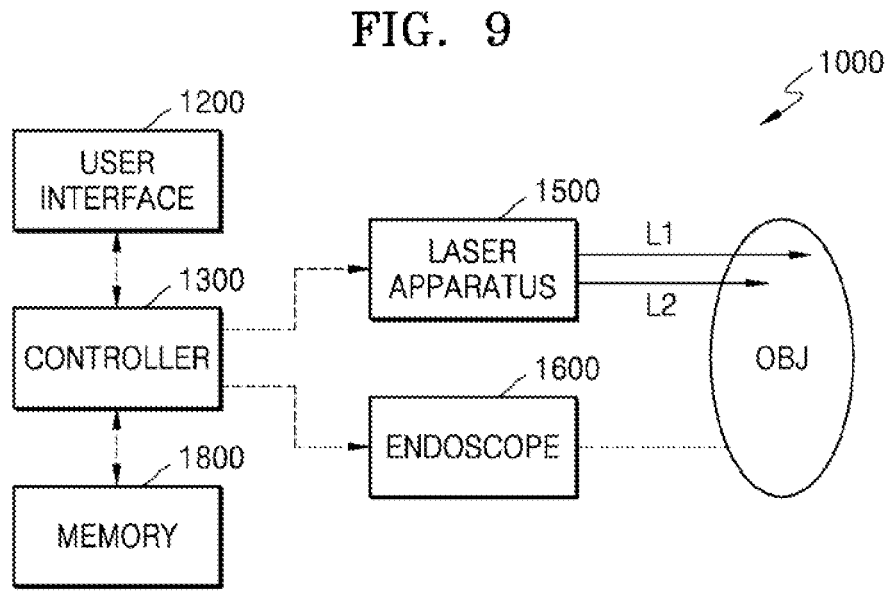
FIG. 9 is a schematic block diagram showing the configuration of a treatment apparatus according to an embodiment.
Figure 10:
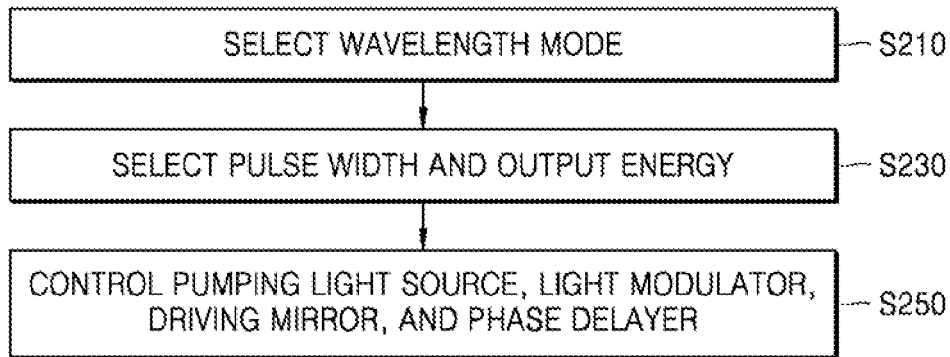
FIG. 10 is a schematic flowchart showing the driving of the treatment apparatus of FIG. 9.

FIG. 9 is a schematic block diagram showing the configuration of a treatment apparatus according to an embodiment. FIG. 10 is a schematic flowchart showing the driving of the treatment apparatus of FIG. 9.

A treatment apparatus 1000 may include a laser apparatus 1500, and a controller 1300 for driving the laser apparatus 1500. The laser apparatus 1500 may include any one of the laser apparatuses 100, 101, 102, 200, and 201 according to the embodiments described above, or modifications thereof.

The controller 1300 may select a wavelength mode of the laser apparatus 1500 and thus may drive the laser apparatus 1500. The treatment apparatus 1000 may further include an endoscope 1600 for observing the inside of an object OBJ a memory 1800 for storing information used to control the laser apparatus 1500, and a user interface 1200. The user interface 1200 may include a display portion and an input portion. The input portion may include, for example, a keyboard, a touch panel, and the like.

In a treatment using laser light, laser beams of different types and different energies may be necessary depending on the locations or types of blood vessel lesions. For example, while the laser beam L2 of a second wavelength that is a short wavelength is used for a treatment of blood vessel lesions existing in a skin epidermis layer of the object OBJ, the laser beam L1 of a first wavelength that is a long wavelength may be used for a treatment of blood vessel lesions at a deeper position.

The laser apparatus 1500 may output a laser beam of a 1064 nm wavelength that is a long pulse to 60 ms in a flat top mode in which energy is uniform in a single pulse width, and output a laser beam of a 532 nm wavelength in which the width of a pulse train composed of nano-unit pulses implemented to about 40 ms. Also, when the laser beam of a 532 nm wavelength is output, even in a range of 0.3 ms to 0.7 ms that is a relatively short pulse width range in a ms long pulse area, compared to existing equipment that does not implement such range or implement low output energy, a high energy output of a clinically significant is possible.

A laser beam of a 1064 nm wavelength that is a true long pulse laser beam maybe used for toning for improving skin texture, wrinkles, pores, face tone, scar, and the like, removal of deep and thick blood vessels such as leg veins, hair removal, skin elasticity increase, pore reduction, inflammatory acne treatment, acne erythema improvement, skin lifting, skin fine wrinkles removal, and the like.

A laser beam of a 532 nm wavelength is suitable for superficial vascular lesions or pigmented lesions, and may be used for treatments of epidermal pigment, blemishes, pigmentation, flat warts, age spots, freckles, blood vessel removal, flushing, and the like.

A wavelength mode to drive the laser apparatus 1500 is selected according to the above needs (S210), and furthermore, a necessary pulse width or output energy may be selected (S230). A pumping light source, a light modulator, a driving mirror, and a phase delayer included in the laser apparatus 1500 may be controlled according to the selected setting. When the laser apparatus 1500 is configured with only one wavelength mode, the operation S210 may be omitted.

The treatment apparatus 1000 may further include a cooling device (not shown). The cooling device is provided to reduce or remove heat diffused in skin tissues in a laser irradiation process. The cooling device may include air cooling using cold air, cooling using cryogen gas, or a contact cooling device using thermoelectric element or cooling water in a portion where the laser apparatus 1500 contacts the object OBJ. When applying the treatment apparatus 1000 to various clinical cases, by using a cooling device, side effect prevention and sufficient laser energy transfer are possible and furthermore, inconvenience to patents in a treatment process may be reduced.

As the treatment apparatus 1000 includes the laser apparatus 1500 which may exhibit constant beam quality when generating a laser beam of a short wavelength in a wavelength conversion method, or output a multi-wavelength laser beam of excellent quality, treatment effects suitable for the types of lesions may be obtained.

As such, while the disclosure has been particularly shown and described with reference to preferred embodiments using specific terminologies, the embodiments and terminologies should be considered in descriptive sense only and not for purposes of limitation. Therefore, it will be understood by those of ordinary skill in the art that various changes in form and details may be made therein without departing from the spirit and scope of the disclosure as defined by the following claims.

The invention claimed is:

1. A laser apparatus comprising:
a laser generator comprising a laser medium, a pumping light source providing light to the laser medium, a first mirror and a second mirror arranged with the laser medium therebetween, and configured to generate a laser beam of a first wavelength;
a secondary harmonic wave generator configured to generate a laser beam of a second wavelength from the laser beam of the first wavelength;
a light modulator arranged between the laser medium and the secondary harmonic wave generator and configured to adjust a pulse width of the laser beam of the first wavelength; and
an output adjustor configured to adjust an output of the laser beam of the second wavelength generated in the secondary harmonic wave generator,
wherein the secondary harmonic wave generator comprises the second mirror, a non-linear medium, and a third mirror facing the second mirror with the non-linear medium therebetween.

2. The laser apparatus of claim 1, wherein the output adjustor comprises:
a phase delayer configured to change a phase of the laser beam of the second wavelength; and
a polarizer arranged on an optical path passing the phase delayer.

3. The laser apparatus of claim 2, wherein the phase delayer comprises an element that adjusts a degree of a phase delay of incident light, by being rotated according to an input signal.

4. The laser apparatus of claim 3, further comprising a driving mirror arranged on an optical path between the secondary harmonic wave generator the output adjustor, and configured to be driven to be on or out of the optical path to allow the laser beam of the second wavelength to be output by passing through the output adjustor or not.

5. The laser apparatus of claim 1, wherein a polarizer is not arranged on a path between the laser medium and the non-linear medium, and
the laser beam of the first wavelength is incident on the non-linear medium in a non-polarization state.

6. The laser apparatus of claim 1, wherein the laser medium generates a laser beam of a 1064 nm wavelength, and
the secondary harmonic wave generator generates a laser beam of a 532 nm wavelength.

7. A laser apparatus comprising:

a laser generator comprising a first mirror, a laser medium, and a pumping light source that provides light to the laser medium, the laser generator being configured to a laser beam of a first wavelength;

a secondary harmonic wave generator configured to generate a laser beam of a second wavelength from the laser beam of the first wavelength, and comprising a non-linear medium, and a second mirror and a third mirror arranged with the non-linear medium therebetween;

a light modulator arranged between the laser medium and the secondary harmonic wave generator and configured to adjust a pulse width of the laser beam of the first wavelength;

a driving mirror arranged on an optical path between the laser medium and the light modulator, having a total reflection surface inclined with respect to the optical path, and configured to be driven to be on or out of the optical path;

a fourth mirror arranged on an optical path along which light reflected from the driving mirror travels;

an output adjustor configured to adjust an output of the laser beam of the second wavelength generated in the driving secondary harmonic wave generator; and one or more optical path adjustment optical elements configured to match an output path when the laser beam of the first wavelength or the laser beam of the second wavelength is output according to a location of the driving mirror, wherein, when the driving mirror is on the optical path, the first mirror and the fourth mirror form a resonance path to generate the laser beam of the first wavelength, and when the driving mirror is moved out of the optical path, the first mirror and the third mirror form a resonance path to generate the laser beam of the first wavelength.

8. The laser apparatus of claim 7, wherein the one or more optical path adjustment optical elements are configured to output the laser beam of the first wavelength when the driving mirror is on the optical path, and the laser beam of the second wavelength when the driving mirror is moved out of the optical path.

9. The laser apparatus of claim 7, wherein the one or more optical path adjustment optical elements comprise:

a fifth mirror configured to reflect light having transmitted the fourth mirror in a perpendicular direction;

a sixth mirror configured to reflect light having passed through the output adjustor in the perpendicular direction; and a first beam splitter configured to transmit light reflected from the fifth mirror, and reflect light reflected from the sixth mirror in the perpendicular direction.

10. The laser apparatus of claim 7, wherein the one or more optical path adjustment optical elements comprise:

a seventh mirror and an eighth mirror arranged between the light modulator and the secondary harmonic wave generator and configured to sequentially and respectively reflect incident light in a perpendicular direction;

a ninth mirror and a tenth mirror arranged between the secondary harmonic wave generator and the output adjustor and configured to sequentially and respectively reflect incident light in the perpendicular direction; and a second beam splitter configured to reflect light having transmitted the fourth mirror in the perpendicular direction and transmit light having passed through the output adjustor.

11. The laser apparatus of claim 7, further comprising:

an optical fiber arranged on the output path; and a focusing lens arranged on the output path and configured to focus light on the optical fiber.

12. The laser apparatus of claim 7, wherein the output adjustor comprises:

a phase delayer configured to change a phase of the laser beam of the second wavelength; and a polarizer arranged on the optical path after the phase delayer.

13. The laser apparatus of claim 7, wherein no polarizer is arranged between the laser medium and the non-linear medium, and the laser beam of the first wavelength is incident on the non-linear medium in a non-polarization state.

14. A treatment apparatus comprising:

a laser apparatus according to claim 7; and a controller configured to select a wavelength mode of the laser apparatus and drive the laser apparatus in a selected mode.

15. The treatment apparatus of claim 14, wherein the laser beam of the second wavelength is used for treatment of superficial vascular lesions or pigmented lesions, and the laser beam of the first wavelength is used for treatment of lesions at a relatively deep position.

16. The treatment apparatus of claim 14, wherein the laser beam of the second wavelength comprises a laser beam of a 532 nm wavelength, and is used for any one of epidermal pigment, blemishes, pigmentation, flat warts, age spots, freckles, blood vessel removal, and flushing.

17. The treatment apparatus of claim 14, wherein the laser beam of the first wavelength comprises a laser beam of a 1064 nm wavelength, and is used for any one of toning for improving skin texture, wrinkles, pores, face tone, or scar, vein vessel removal, hair removal, acne erythema improvement, pore shrinkage, skin lifting, skin fine wrinkle removal, and inflammatory acne treatment.

* * * * *